United States Patent [19]

Hagedorn et al.

[11] Patent Number: 5,463,068

[45] Date of Patent: Oct. 31, 1995

[54] PROCESS FOR DESULPHURIZING ORGANIC MERCAPTO AND/OR DISULPHIDE COMPOUNDS

[75] Inventors: Ferdinand Hagedorn; Helmut Fiege; Hans-Joachim Traenckner, all of Leverkusen, Germany

[73] Assignee: Bayer Aktiengesellschaft, Leverkusen, Germany

[21] Appl. No.: 255,024

[22] Filed: Jun. 7, 1994

[30] Foreign Application Priority Data

Jun. 14, 1993 [DE] Germany ............. 43 19 574.1

[51] Int. Cl.⁶ ............. C07D 277/82; C07D 235/04
[52] U.S. Cl. ............. 548/152; 548/304.4
[58] Field of Search ............. 548/262, 174, 548/177, 152

[56] References Cited

U.S. PATENT DOCUMENTS

| | | | |
|---|---|---|---|
| 2,402,642 | 6/1946 | Lazier et al. | 548/152 X |
| 2,610,190 | 9/1952 | Chao et al. | 548/152 X |
| 4,977,174 | 12/1990 | Stein et al. | 514/382 |

FOREIGN PATENT DOCUMENTS 263891  7/1989  Czechoslovakia ............. 548/152 X

OTHER PUBLICATIONS

"The Action of Raney Nickel on Organic Sulfur Compounds", H. Hauptmann et al, Jun. 3, 1961, pp. 347–404.

Org. Reactions, vol. 12, 1962, Chapter 5, "Desulfurization with Raney Nickel", G. R. Pettit et al, pp. 356–529.

Acta Chem. Scan., vol. 16, No. 4, 1962; "Reduction of 2–mercaptobenzothiazole to benzothiazole", B. Weibull, p. 1052.

The Baker Laboratory of Chemistry at Cornell University, pp. 718–725; "Benzothiazoles. II. Nuclear Chlorination in the Herz Process", A. T. Blomquist et al, Apr. 23, 1947. *Journal of Organic Chemistry*. vol. 12, pp. 718–725 (1947).

*Primary Examiner*—Floyd D. Higel
*Attorney, Agent, or Firm*—William C. Gerstenzang; Sprung Horn Kramer & Woods

[57] ABSTRACT

Organic compounds of reduced sulphur content and sulphur-free organic compounds can be prepared from organic mercapto and/or disulphide compounds in a particularly advantageous manner by hydrogenolytic elimination of hydrogen sulphide if the elimination of hydrogen sulphide is carried out in the presence of an organic solvent by means of an aqueous, non-oxidizing, strong acid and elemental iron, aluminium and/or zinc in the presence of catalytic amounts of nickel and/or cobalt.

9 Claims, No Drawings

PROCESS FOR DESULPHURIZING ORGANIC MERCAPTO AND/OR DISULPHIDE COMPOUNDS

The present invention relates to a process for preparing organic compounds of reduced sulphur content and sulphur-free organic compounds from organic mercapto and/or disulphide compounds by hydrogenolytic elimination of hydrogen sulphide.

Desulphurization of mercapto compounds with Raney nickel forms the subject-matter of a multitude of publications (see, for example, Chem. Rev. 62, 347–404 (1962) and Org. Reactions 12,356–529 (1962)). These are methods in which the actual agent is hydrogen which adheres to the Raney nickel or is formed by basic hydrolysis of Raney alloys. These reactions are in general carried out in the alkaline to neutral range. This is why a very large excess of Raney nickel is necessary.

The reduction of 2-mercaptobenzothiazole with iron powder in an acetic acid/ethanol/water mixture gave benzothiazole in a yield of only 51% of theory (see Acta Chem. Scand. 16(4), 1052 (1962)).

Other hydrogenating methods for preparing benzothiazole from 2-mercaptobenzothiazole (see, for example, U.S. Pat. No. 2,402,642 and CS-A 263,891) use cobalt trisulphide as the catalyst and require high pressures and solvents which can only be handled under extensive safety precautions (for example 1,4-dioxane) if high yields are to be obtained. The yields in these methods are in the range from 80 to 99% of theory.

A process for preparing organic compounds of reduced sulphur content and sulphur-free organic compounds from organic mercapto and/or disulphide compounds by hydrogenolytic elimination of hydrogen sulphide has now been found, which process is characterized in that the elimination of hydrogen sulphide is carried out in the presence of an organic solvent by means of an aqueous, nonoxidizing, strong acid and elemental iron, aluminium and/or zinc in the presence of catalytic amounts of nickel and/or cobalt.

A wide range of organic mercapto and disulphide compounds can be used in the process according to the invention. Preference is given to the use of cyclic, nitrogen-containing mercapto and disulphide compounds in which the nitrogen atom or the nitrogen atoms can be part of the ring or can be attached to the ring as substituents. The rings can be, for example, monocyclic or bicyclic systems in which, for example, in each case 5 or 6 atoms form a ring.

Particularly preferably, the materials used for the process according to the invention are mercapto and disulphide compounds of benzothiazoles and benzimidazoles, such as 2-mercapto-benzothiazole, 2-mercaptobenzimidazole and 2,2'-bis-(benzothiazolyl) disulphide.

In the process according to the invention, the mercapto or disulpide groups are in general removed from the materials used in a very selective manner. Thus, for example, mercaptobenzothiazoles and bis-(benzothiazolyl) disulphides give the corresponding benzothiazoles, virtually without any further desulphurization of the benzothiazole (for example to give N-methylaniline). If, for example, mercapto or disulphide compounds of benzimidazoles are used in the process according to the invention, the corresponding benzimidazoles are obtained.

Examples of suitable organic solvents for the process according to the invention are those which are inert in the reaction mixture and are miscible with strong aqueous acids. Examples of suitable solvents are aliphatic alcohols having 1–6 C atoms and carboxylic acids having 1 to 4 C atoms. Preference is given to methanol, ethanol, isopropanol and acetic acid, in particular methanol. The solvents can be used, for example, in amounts of 0.5 to 50 ml, relative to 1 gram of organic mercapto or disulphide compound used. It is not necessary to add enough solvent for obtaining a clear solution of the material used since the process according to the invention can also be carried out if the material used is present entirely or in part in suspended form.

Aqueous, non-oxidizing, strong acids include in particular those which dissolve iron, aluminium and/or zinc with evolution of hydrogen and in which no sparingly soluble sulphides of iron, aluminium and/or zinc are formed under the reaction conditions. Preference is given to aqueous mineral acids, in particular to aqueous hydrochloric acid and aqueous sulphuric acid, for example 5–40% strength by weight aqueous hydrochloric acid and 5–40% strength by weight aqueous sulphuric acid. Particular preference is given to 25–40% strength by weight aqueous hydrochloric acid.

Advantageously, the acid is used at least in the amount required by theory for evolving with the elemental iron, aluminium and/or zinc used enough hydrogen, as required by theory, for converting the mercapto and disulphide groups present in the material used into hydrogen sulphide. Preferably, an excess of acid is used, for example up to twice the amount required by theory.

Iron, aluminium and/or zinc are used in elemental and, preferably, in finely divided form. Preference is given to iron and aluminium, in particular iron filings, iron powder, atomized iron and/or aluminium powder.

For example, 1–12 mol of iron, aluminium and/or zinc, relative to 1 mol of mercapto or disulphide compound, can be used. The amount of iron, aluminium and/or zinc used is preferably 1–2 mol, relative to 1 mol of mercapto compound used, and preferably 2–4 mol, relative to 1 mol of disulphide compound used. Larger amounts of metals can be advantageous especially if the metals are not present in finely divided form.

It is advantageous to ensure a good contact between the hydrogen being evolved and the mercapto or disulphide compounds used while the process according to the invention is being carried out. This can be effected, for example, by applying stirring or bubble-cap column techniques known per se.

It is an essential feature of the process according to the invention that it is carried out in the presence of catalytic amounts of nickel and/or cobalt. Nickel and/or cobalt can be added in metallic form or in the form of salts. Preference is given to the use of elemental nickel or elemental cobalt in the form of Raney nickel or Raney cobalt. Of these, particular preference is given to used catalysts, i.e. Raney nickel, Raney cobalt or Raney nickel/cobalt which has already been used as catalyst in other processes, for example in catalytic hydrogenations using elemental hydrogen. Specifically Raney nickel can also be added in the form of Raney nickel/iron. Nickel and/or cobalt in the form of salts can be used, for example, in the form of chlorides.

Relative to 1 mol of elemental iron, aluminium and/or zinc used, it is possible to use, for example, 0.01–0.5 mol of nickel and/or cobalt in elemental form or in the form of salts. Preferably, this amount is 0.01–0.3 mol.

The process according to the invention can be carried out, for example, at temperatures in the range from 0°–120° C. Preference is given to temperatures in the range from 40°–100° C. It is particularly preferred to use a solvent boiling under reflux.

The process according to the invention can be carried out at atmospheric pressure, elevated pressure or reduced pressure. Preferably, the reaction is carried out at atmospheric pressure. Reduced or elevated pressure, for example in the range from 0.1–5 bar, may be of interest if it is desired to carry out the reaction in a solvent boiling under reflux but at a temperature other than the boiling point of the particular solvent at atmospheric pressure.

The process according to the invention can be carried out, for example, in such a manner that the mercapto or disulphide compound is introduced first together with the solvent and elemental iron, aluminium and/or zinc, and nickel and/or cobalt in metallic form or in the form of salts, the mixture is then heated to the desired reaction temperature, and the acid is then run in with vigorous stirring. The evolving hydrogen sulphide can be collected and disposed of in a manner known per se, for example by washing with aqueous sodium hydroxide solution or by feeding it into a Claus process for preparing elemental sulphur.

After the addition of acid is complete, it is advantageous to continue stirring at the reaction temperature at least until evolution of hydrogen has come to an end. If excess elemental iron, aluminium and/or zinc is still present, any nickel and/or cobalt present in the reaction mixture in dissolved form is deposited thereupon. Workup of the reaction mixture can be such that first the liquid phase is separated off from any metal residue which may be present, the solvent is recovered by distillation, and the product obtained is isolated by steam distillation or extraction with a suitable solvent. The metal residue which has been separated off can be reused. Since it contains virtually the entire nickel and/or cobalt used, this metal does not have to be constantly introduced from the outside.

This embodiment of the present invention described in detail can be varied in many ways. For example, the process according to the invention can also be carried out continuously or batchwise.

In general, the process according to the invention produces products of reduced sulphur content and/or sulphur-free products from organic mercapto and disulphide compounds in yields of more than 90% of theory.

Compared with the hydrogenation methods of the prior art, the process according to the invention has the important advantages that it can be carried out at atmospheric pressure and only requires catalytic amounts of nickel and/or cobalt. A further advantage is the mild reaction temperature which can be selected, for example, in the range between room temperature and the boiling temperature of the reaction medium used. A surprising feature are the high yields and selectivities obtainable despite the mild reaction conditions. The biggest advantage of the present invention is the fact that, in contrast to the previous method, only catalytic amounts of nickel and/or cobalt are required, which is very desirable for ecological reasons. Nevertheless, the yields are high and, for example, clearly more favourable than in the procedure which uses only iron.

The experimental examples which follow illustrate the process according to the invention without limiting it thereto.

EXAMPLE 1

87.9 g of 2-mercaptobenzothiazole, 111.7 g of iron filings and 9.5 g of nickel chloride ($NiCl_2 \times 6H_2O$) were suspended in 250 ml of methanol. The mixture was heated to boiling under reflux (about 70° C.) with stirring, and 165 ml of concentrated aqueous hydrochloric acid were then added dropwise over a period of 2 hours. The evolving hydrogen sulphide was trapped in a downstream sodium hydroxide washing solution. The mixture was then additionally stirred at 70° C. for 1 hour, followed by cooling, the undissolved metal residue was separated off, and the clear solution obtained was examined by HPLC analysis, which showed a yield of 64.7 g of benzothiazole, which corresponds to 96% of theory.

EXAMPLE 2

16.7 g of 2-mercaptobenzothiazole, 13.6 g of zinc dust and 11.8 g of nickel chloride ($NiCl_2 \times 6H_2O$) were suspended in 250 ml of methanol, and the mixture was heated to 70° C. with stirring. 50 ml of concentrated aqueous hydrochloric acid were added dropwise to the refluxing mixture at 70° C. over a period of 2 hours, during which the hydrogen sulphide gas formed was trapped in a downstream sodium hydroxide washing solution. After an additional stirring time of 30 minutes, undissolved metal residue was separated off, and the solution obtained was subjected to HPLC analysis, which showed a benzothiazole content of 12.5 g, which corresponds to a yield of 90.3% of theory.

EXAMPLE 3

16.6 g of bis-(benzothiazolyl) disulphide, 22.4 g of iron filings and 11.8 g of nickel chloride ($NiCl_2 \times 6H_2O$) were suspended in 250 ml of methanol. The mixture was heated to 70° C. with stirring, and 50 ml of concentrated aqueous hydrochloric acid were added dropwise to the refluxing mixture over a period of 2 hours. The evolving hydrogen sulphide was trapped in a sodium hydroxide washing solution. The reaction mixture was additionally stirred at 70° C. for 30 minutes. After cooling, the mixture was filtered off with suction, and 11.5 g of metallic residue were obtained. HPLC analysis of the separated solution showed the presence of 12.7 g of benzothiazole, which corresponds to 94% of theory.

EXAMPLE 4

15.0 g of 2-mercaptobenzimidazole, 22.4 g of iron filings and 11.8 g of nickel chloride ($NiCl_2 \times 6H_2O$) were suspended in 250 ml of methanol, and the mixture was heated with stirring until the methanol boiled under reflux. 50 ml of concentrated aqueous hydrochloric acid were then added dropwise over a period of 2 hours, and the evolving hydrogen sulphide was trapped in a sodium hydroxide washing solution. The mixture was additionally stirred at 70° C. for 30 minutes, cooled to room temperature, and the metallic residue was separated off by suction filtration. According to HPLC analysis, the remaining solution contained 10.9 g of benzimidazole, which corresponds to 1.9% of theory.

EXAMPLE 5

87.9 g of 95% pure mercaptobenzothiazole, 111.7 g of iron filings and 3 g of used Raney nickel catalyst were first introduced into a stirred flask, and the mixture was heated in 250 ml of methanol to the reflux temperature with stirring. 165 ml of concentrated aqueous hydrochloric acid were added dropwise at 70° C. over a period of 2 hours, and the evolving hydrogen sulphide was trapped in an aqueous sodium hydroxide solution. The mixture was additionally stirred at 70° C. for 1 hour, then cooled to room temperature and filtered off with suction. The filtrate and the wash consisting of methanol and water were combined and examined by HPLC analysis. 65.9 g of benzothiazole were present, which corresponds to a yield of 97.6% of theory.

EXAMPLE 6

87.9 g of 95% pure 2-mercaptobenzothiazole, 111.7 g of iron filings, 11.8 g of nickel chloride ($NiCl_2 \times 6H_2O$) and 250 ml of methanol were first introduced into a stirred flask, and the mixture was heated to the reflux temperature with stirring. 165 ml of conc. aqueous hydrochloric acid were added dropwise at 70° C. over a period of 2 hours, and the evolving hydrogen sulphide was trapped in aqueous sodium hydroxide solution. The mixture was additionally stirred at 70° C. for 1 hour and then diluted with 200 ml of water. 200 ml of methanol were distilled off. The remaining mixture was brought to a pH of 5.6 with aqueous sodium hydroxide solution and steam distilled. The steam distillate was extracted with toluene. Removal of the solvent by distillation gave 66.3 g of crude, colourless benzothiazole, 93.7% pure (GC), which corresponds to a yield of 92% of theory, having a residual toluene content of 5.3%.

What is claimed is:

1. A process for preparing organic compounds of reduced sulphur content and sulphur-free organic compounds from organic mercapto compounds, disulphide compounds or both in yields of more than 90% of theory by hydrogenolytic elimination of hydrogen sulphide, comprising carrying out the elimination of hydrogen sulphide in the presence of an organic solvent by means of an aqueous, non-oxidizing, strong acid selected from the group consisting of aqueous hydrochloric acid and aqueous sulphuric acid, and elemental iron, aluminium, or zinc or mixtures thereof in the presence of catalytic amounts of nickel, cobalt a mixture thereof.

2. The process of claim 1, in which a nitrogen-containing mercapto compound disulphide compound or a mixture thereof is used.

3. The process of claim 1, in which an aliphatic alcohol having 1–6 C atoms or a carboxylic acid having 1–4 C atoms is used as the organic solvent.

4. The process of claim 1, in which the organic solvent is used in an amount of 0.5–50 ml, relative to 1 g of the organic mercapto compound disulphide compound or a mixture thereof used.

5. The process of claim 1, in which the aqueous non-oxidizing, strong acid is used at least in the amount required, with the elemental iron, aluminium and/or zinc used, to evolve enough hydrogen to convert the mercapto and disulphide groups present in the material used into hydrogen sulphide.

6. The process of claim 1, in which elemental iron, aluminium, zinc or a combination thereof is used in finely divided form.

7. The process of claim 1, in which 1 to 12 mol of elemental iron, aluminium, zinc or a combination thereof is used per mole of mercapto or disulphide compound.

8. The process of claim 1, in which nickel, cobalt or a mixture thereof is used in metallic form or in the form of their salts and in an amount of 0.01–0.5 mol of nickel, cobalt or nickel and cobalt per mole of elemental iron, aluminium, zinc or mixtures thereof used.

9. The process of claim 1, which is carried out at a temperature in the range of 0° to 120° C.

* * * * *

UNITED STATES PATENT AND TRADEMARK OFFICE
CERTIFICATE OF CORRECTION

PATENT NO.   : 5,463,068
DATED        : October 31, 1995
INVENTOR(S)  : Hagedorn, et al.

It is certified that error appears in the above-indentified patent and that said Letters Patent is hereby corrected as shown below:

Col. 5, line 28, After " cobalt " insert -- or --

Signed and Sealed this

Sixteenth Day of April, 1996

Attest:

BRUCE LEHMAN

Attesting Officer

Commissioner of Patents and Trademarks